US005955449A

United States Patent [19]
Armstrong et al.

[11] Patent Number: 5,955,449
[45] Date of Patent: *Sep. 21, 1999

[54] DIAGNOSIS AND TREATMENT OF BACTERIAL DYSENTERY

[75] Inventors: Glen D. Armstrong, Edmonton, Canada; Robert M. Ratcliffe, Carlsbad, Calif.

[73] Assignee: SYNSORB Biotech Inc., Calgary, Canada

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/868,929

[22] Filed: Jun. 4, 1997

Related U.S. Application Data

[60] Continuation of application No. 08/453,775, May 30, 1995, Pat. No. 5,679,653, which is a division of application No. 08/126,645, Sep. 27, 1993, Pat. No. 5,620,858, which is a continuation of application No. 07/778,732, Oct. 18, 1991, abandoned.

[51] Int. Cl.[6] .................. A61K 31/70; A61K 31/715; A61K 31/695
[52] U.S. Cl. .................. 514/53; 514/25; 514/54; 514/61; 514/63
[58] Field of Search .................. 514/54, 53, 61, 514/25, 63; 536/123, 123.1, 123.13

[56] References Cited

U.S. PATENT DOCUMENTS

| | | | |
|---|---|---|---|
| 4,347,244 | 8/1982 | Mynard et al. | 514/25 |
| 4,464,360 | 8/1984 | Leffler et al. | 514/53 |
| 4,665,060 | 5/1987 | Mardh et al. | 514/61 |
| 4,863,852 | 9/1989 | Wilkins et al. | 435/7.25 |
| 4,946,943 | 8/1990 | Bloch | 530/377 |
| 5,484,773 | 1/1996 | Heerze et al. | 514/23 |
| 5,620,858 | 4/1997 | Armstrong et al. | 435/7.8 |
| 5,679,653 | 10/1997 | Armstrong et al. | 514/53 |

OTHER PUBLICATIONS

Acheson et al., "Enzyme–Linked Immunosorbent Assay for Shiga Toxin and Shiga–like Toxin II Using P1 Glycoprotein from Hydatid Cysts" *The Journal of Infectious Diseases* 161:134–137 (1990).
Ashkenazi, et al, "Rapid Method to Detect Shiga Toxin and Shiga–Like Toxin I Based on Binding to Globotriosyl Ceramide (GB$_3$), Their Natural Receptor", *J. Clin. Microb.* 27(6):1145–1150 (1989).
Boyd et al., "Verotoxin Receptor Glycolipid in Human Renal Tissue" *Nephron* 51:207–210 (1989).
Brown, et al., "Digalactosyl–Containing Glycolipids as Cell Surface Receptors for Shiga Toxin of *Shigella dysenteriae* I and Related Cytotoxins of *Escherichia coli*", *Review of Infectious Diseases* 13(4):S298–S303 (1991).

Calderwood et al., "Nucleotide sequence of the Shiga–like toxin genes of *Escherichia coli*", *Proceedings of the National Academy of Science USA* 84:4364–4368 (1983).
Cimolai et al., "Influence of Antidarrheal and Antimicrobial Medications on the Hemorrhagic Colitis Associated with Hemolytic–Uremic Syndrome", *The Journal of Pediatrics* 117(4):676 (1990).
Cohen et al., "Roles of Globotriosyl– and Galabiosylceramide in Verotoxin Binding and High Affinity Interferon Receptor", *Journal of Biological Chemistry* 262(35):17088–17091 (1987).
Daikoku et al., "Partial Purification and Characterization of the Enterotoxin Produced by *Camplyobacter jejuni*", *Infection and Immunity* 58(8):2414–2419 (1990).
DeGrandis et al., "Globotetraosylceramide is Recognized by the Pig Edema Disease Toxin", *Journal of Biological Chemistry* 264(21):12520–12525 (1989).
Donohue–Rolfe et al., "Purification of Shiga Toxin and Shiga–Like Toxins I and II by Receptor Analog Affinity Chromatography with Immobilized P1 Glycoprotein and Production of Cross–Reactive Monoclonal Antibodies" *Infection and Immunity* 57(12):3888–3893 (1989).
Dubey et al., "Purification of EI Tor Cholera Enterotoxins and Comparisons with Classical Toxin", *Journal of General Microbiology* 136:1839–1837 (1990).
Galili et al., "The Subtlety of Immune Tolerance in Man as Demonstrated by Crossreactivity Between Natural Anti–Gal and Anti–B Antibodies" *Journal of Experimental Medicine* 165:693–704 (1987).
Gannon et al., "Molecular Cloning and Nucleotide Sequence of Another Variant of the *Escherichia coli* Shiga–ke Toxin II Family", *Journal General Microbiol.* 136:1125–1135 (1990).
Head et al., "Purification and Characterization of Verocytotoxin 2", *FEMS Microbiology Letters* 51:211–216 (1988).
Ito et al., "Cloning and Nucleotide Sequencing of Vero Toxin 2 Variant Genes from *Escherichia coli* 091:H21 Isolated from a Patient with the Hemolytic Uremic Syndrome", *Microbial Pathogenesis* 8:47–60 (1990).
Jacewicz et al., "Pathogenesis of Shigella Diarrhea" *Journal of Experimental Medicine*163:1391–1404 (1986).
Jackson et al., "Nucleotide sequence analysis of the structural genes for Shiga–like toxin I Encoded by Bacteriophage 933J from *Escherichia coli*", *Microbial Pathogenesis* 2:147–153 (1987).
Karlsson, "Animal Glycolipids as Attachment Sites for Microbes" *Chemistry and Physics of Lipids,* 42:153–172 (1986).

(List continued on next page.)

*Primary Examiner*—Howard C. Lee
*Attorney, Agent, or Firm*—Burns, Doane, Swecker & Mathis, L.L.P.

[57] ABSTRACT

Diagnostic and therapeutic compositions which comprise the αGal(1–4)βGal subunit are described. These compositions permit the rapid diagnosis and treatment of enteric infections caused by *E. coli* that produce shiga-like toxins (SLT).

10 Claims, 5 Drawing Sheets

OTHER PUBLICATIONS

Karlsson, "Animal Glycosphingolipids as Membrane Attachment Sites for Bacteria[1]", *Annu. Rev. Biochem.* 58:309–50 (1989).

Karmali et al., Sensitive Method for Detecting Low Numbers of Verotoxin–Producing *Escherichia coli, Journal of Clinical Microbiology* 22(4):614–619 (1988).

Lemieux, et al., The Properties of a "Synthetic" Antigen Related to the Human Blood–Group Lewis a *J. Am. Chem. Soc.* 97:4076–4083 (1975).

Lenz et al., "Possible Role of Gangliosides in the Interaction of Colony–Stimulating Factor with Granulocyte–Macrophage Progenitor Cells" *Chemical Abstracts* 103:176 (1985) (abstract No. 135938c).

Lindberg et al., "Identification of the Carbohydrate Receptor for Shiga Toxin Produced by Shigella Dysenterae Type 1" *Journal of Biological Chemistry* 262(4):1779–1785 (1987).

Lingwood et al., "Glycolipid Binding of Purified and Recombinant *Escherichia coli* Produced Verotoxin in Vitro", *Journal of Biological Chemistry* 262:8834–8839 (1987).

Maniar et al., "Detection of Verotoxin in Stool Specimens", *Journal of Clinical Microbiology* 28(1):134–135 (1990).

Oku et al., Purification and some Properties of a Vero Toxin from a Human Strain *Microbial Pathogenesis* 6:113–122 (1989).

Parikh et al., "Gangliside–Agarose and Cholera Toxin" *Methods in Enzymology* 34:610–619 (1974).

Pellizarri, et al. "Binding of Verocytotoxin I to its Receptor Is Influenced by Differences in Receptor Fatty Acid Content" *Biochem.* 31:1363–1370 (1992).

Robson et al., "Influence of Antidarrheal and Antimicrobial Medications on the Hemorrhagic Colitis Associated with Hemolytic–Uremic Syndrome" *The Journal of Pediatrics* 117(4):675–676 (1990).

Samuel et al., "Comparison of the Glycolipid Receptor Specificities of Shiga–Like Toxin Type II and Shiga–Like Toxin Type II Variants", *Infection and Immunity* 58(3):611–618 (1990).

Schmitt et al., "Two Copies of Shiga–Like Toxin II–Related Genes Common in Enterohemorrhagic *Escherichia Coli* Strains are Responsible for the Antigenic Heterogeneity of the 0157:H– Strain E32511", *Infection and Immunity* 59(3):1065–1073 (1991).

Scotland et al., "Two Distinct Toxins Active on Vero Cells from *Escherichia coli* 0157", *The Lancet* II:885–886 (1985).

Strockbine et al., Cloning and Sequencing of the Genes for Shiga Toxin from *Shigella Dysente* Type 1:, *Journal of Bacteriology* 170(3):1116–1122 (1988).

Tayot et al., "Isolation of Cholera Toxin by Affinity Chromatography on Porous Silica Beads with Covalently Coupled Ganloiside $G_{M1}$", *Advances in Experimental Medicine and Biology* 125:471–478 (1980).

Tayot et al., "Receptor–Specific Large–Scale Purification of Cholera Toxin on Silica Beads Derivatized with $LysoG_{M1}$ Ganglioside" *European Journal of Biochemistry* 113:249–258 (1981).

Waddell et al., "Globotriosyl Ceramide is Specifically Recognized by the *Escherichia coli* Veroclytotoxin 2" *Biochemical and Biophysical Research Communications* 152(2):674–679 (1988).

Waddell et al., "Induction of Verotoxin Sensitivity in Receptor–Deficient Cell Lines Using the Receptor Glycolipid Globotriosylceramide" *Proceeding of the National Academy of Science USA* 87:7898–7901 (1990).

Weinstein et al, "Cloning and Sequencing of a Shiga–Like Toxin Type II Variant from an *Escherichia coli* Strain Responsible for Edema Disease of Swine", *Journal of Bacteriology* 170(9):4233–4230 (1988).

DIAGNOSIS AND TREATMENT OF BACTERIAL DYSENTERY

This application is a continuation of application Ser. No. 08/453,775, filed May 30, 1995, now U.S. Pat. No. 5,679,653, which in turn is a divisional of application Ser. No. 08/126,645, filed Sep. 27, 1993, now U.S. Pat. No. 5,620,858, which further, in turn, is a continuation of application Ser. No. 07/778,732, filed Oct. 18, 1991 and now abandoned.

TECHNICAL FIELD

The invention relates to diagnosis and treatment of diarrhea caused by bacterial infection. More specifically, the invention concerns detection and neutralization of shiga-like toxins (SLT) associated with enteric bacterial infection.

BACKGROUND ART

Diarrhea caused by strains of pathogenic *E. coli* has been found to be associated with the production of a variety of enterotoxins. Some pathogenic *E. coli* enterohemorrhagic produce enterotoxins that are closely related to the shiga toxin associated with Shigella-caused dysentery. The first member of the family of shiga-like toxins (SLT) to be isolated was cytotoxic for African Green Monkey (Vero) cells and was originally called verotoxin. Since its structural similarity to shiga toxin has been established by sequencing of the relevant genes, this toxin is now more commonly called shiga-like toxin I (SLTI). See, for example, Calderwood, S. B., et al., *Proc Natl Acad Sci USA* (1987) 84:4364–4368; Jackson, M. P., et al., *Micro Pathog* (1987) 2:147–153; Strockbine, N. A., et al., *J Bacteriol* (1988) 170:1116–1122.

Additional members of the SLT family have subsequently been isolated that can be distinguished serologically, on the basis of gene sequence or host specificity (Gannon, V. P. J., et al., *J Gen Microbiol* (1990) 136:1125–1135; Weinstein, D. L., et al., *J Bacteriol* (1988) 170:4223–4230; Ito, H., et al., *Microb Pathog* (1990) 8:47–60; Head, S. C., et al., *FEMS Microbiol Lett* (1988) 51:211–216; Schmitt, C. K., et al., *Infect Immun* (1991) 59:1065–1073; Scotland, S. M., et al., *Lancet* (1985) ii:885–886; Oku, Y., et al., *Microb Pathog* (1989) 6:113–122. Various types of SLTII have been described and have been assigned various designations depending on the strain of *E. coli* from which they are isolated and the hosts they inhabit. Thus, variants have been designated SLTII; vtx2ha; SLTIIvh; vtx2hb; SLTIIc; SLTI-Ivp and so forth.

All of the SLT's are multimeric proteins composed of an enzymatic (A) subunit and multiple (B) subunits responsible for toxin binding to receptors on host tissues. The binding B oligomers of SLTI, SLTII and SLTIIvh recognize host cell globoseries glycolipid receptors containing at minimum the disaccharide subunit αGal(1–4)βGal at the non-reducing terminus; SLTIIvp has been shown to bind to the receptors containing this subunit but not necessarily at the non-reducing end (Samuel, J. E., et al., *Infect Immun* (1990) 58:611–618; Boyd, B., et al., *Nephron* (1989) 51:207–210; DeGrandis, S., et al., *J Biol Chem* (1989) 264:12520–12525; Waddell, T., et al., *Biochem Biophys Res Comm* (1988) 152:674–679; Lingwood, C. A., et al., *J Biol Chem* (1987) 262:8834–8839; Waddell, T., et al., *Proc Natl Acad Sci USA* (1990) 87:7898–7901; Cohen, A., et al., *J Biol Chem* (1987) 262:17088–17091; Jacewicz, M., et al., *J Exp Med* (1986) 163:1391–1404; Lindberg, A. A., et al., *J Biol Chem* (1987) 262:1779–1785.

SLT activity has been detected in stool samples of symptomatic patients (Karmali, M. A., et al., *J Clin Microbiol* (1988) 22:614–619; Maniar, A. C., et al., *J Clin Microbiol* (1990) 28:134–135). However, there is difficulty in detecting the presence of SLTs clinically since these are very potent toxins present in low concentrations. In order to assure detection, the SLT present in the sample must be concentrated to enhance the reliability of the assay. Present diagnostic procedures are technically demanding, time consuming and of limited practical use in the clinical setting. Thus there is a clear need for improved diagnostic clinically practical and rapid procedures.

Also, antibiotics are not recommended for treatment of enterohemorrhagic *E. coli* infection (Robson, W. L. M., et al., *J Pediatr* (1990) 117:675–676) and the use of antimotility drugs also appears to be counterproductive (Cimolai, N., et al., *J Pediatr* (1990) 117:676. There is, therefore, also a clear need for new and effective therapeutic agents.

It has now been found that artificial substrates containing the αGal(1–4)βGal ($P_1$ disaccharide) subunit and more preferably the αGal(1–4)βGal(1–4)βGlcNAc ($P_1$ trisaccharide) or αGal(1–4)βGal(1–4)βGlc ($P_k$ trisaccharide) subunit are effective in detecting and neutralizing members of the SLT family under conditions necessary to effect recovery of the patient and as such represent novel therapeutic and diagnostic tools in the treatment of *E. coli*-mediated dysentery.

DISCLOSURE OF THE INVENTION

The invention provides compositions and methods that permit practical and effective diagnosis of *E. coli*-caused enterotoxic bacterial infections that present clinically as severe diarrhea, hemorrhagic colitis, hemolytic uremic syndrome or thrombotic thrombocytopenic purpura. The invention also provides compositions useful in the therapy of these and related conditions.

Thus, in one aspect, the invention is directed to a method to simply and rapidly bind to a support shiga-like toxins (SLT) from a biological sample at physiological conditions for diagnostic use, which method comprises contacting said sample with an effective amount of an affinity support wherein the affinity ligand comprises an αGal(1–4)βGal subunit under conditions wherein said SLT is adsorbed to the affinity support; and detecting any SLT bound to the support.

In another aspect, the invention is directed to methods to detect the presence of SLT in a biological sample which method comprises contacting said sample with a composition comprising the αGal(1–4)βGal subunit under conditions wherein said subunit is complexed to any SLT present in the sample and detecting the presence of any complex formed.

In a third aspect, the invention is directed to a method to treat enteric infections caused by microorganisms that produce one or more SLTs, which method comprises administering to a subject in need of such treatment an effective amount of a composition comprising the αGal(1–4)βGal subunit.

In still other aspects, the invention is directed to pharmaceutical compositions which comprise the αGal(1–4)βGal subunit.

B demonstrates that the binding of the SLT toxins occurred within 5 minutes of mixing extracts with the $P_k$ SYNSORB.

Figure 4:
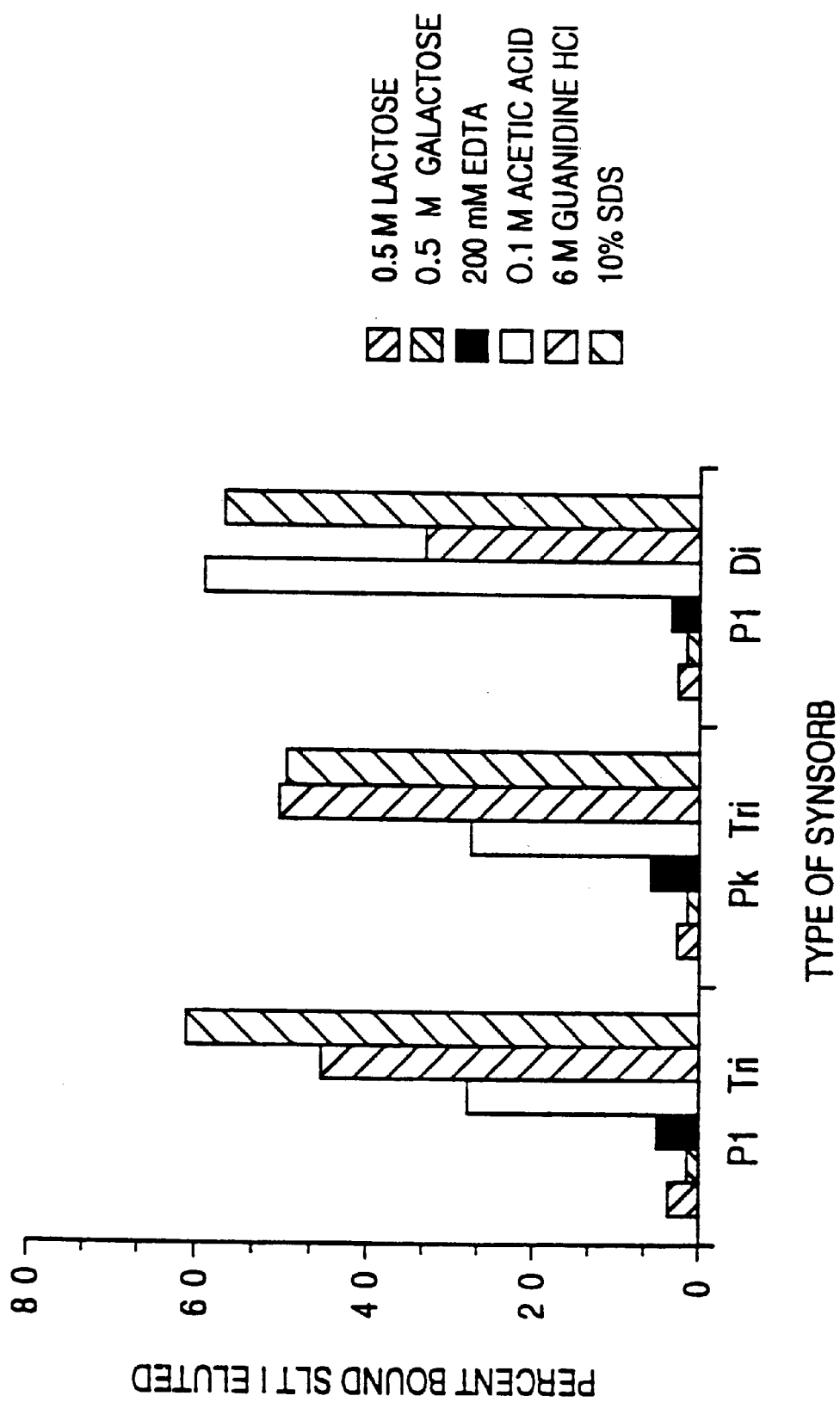

FIG. 4 demonstrates the difficulty in eluting the bound $I^{125}$ labelled SLTI from various SYNSORBs utilizing a variety of eluants.

Figure 5:
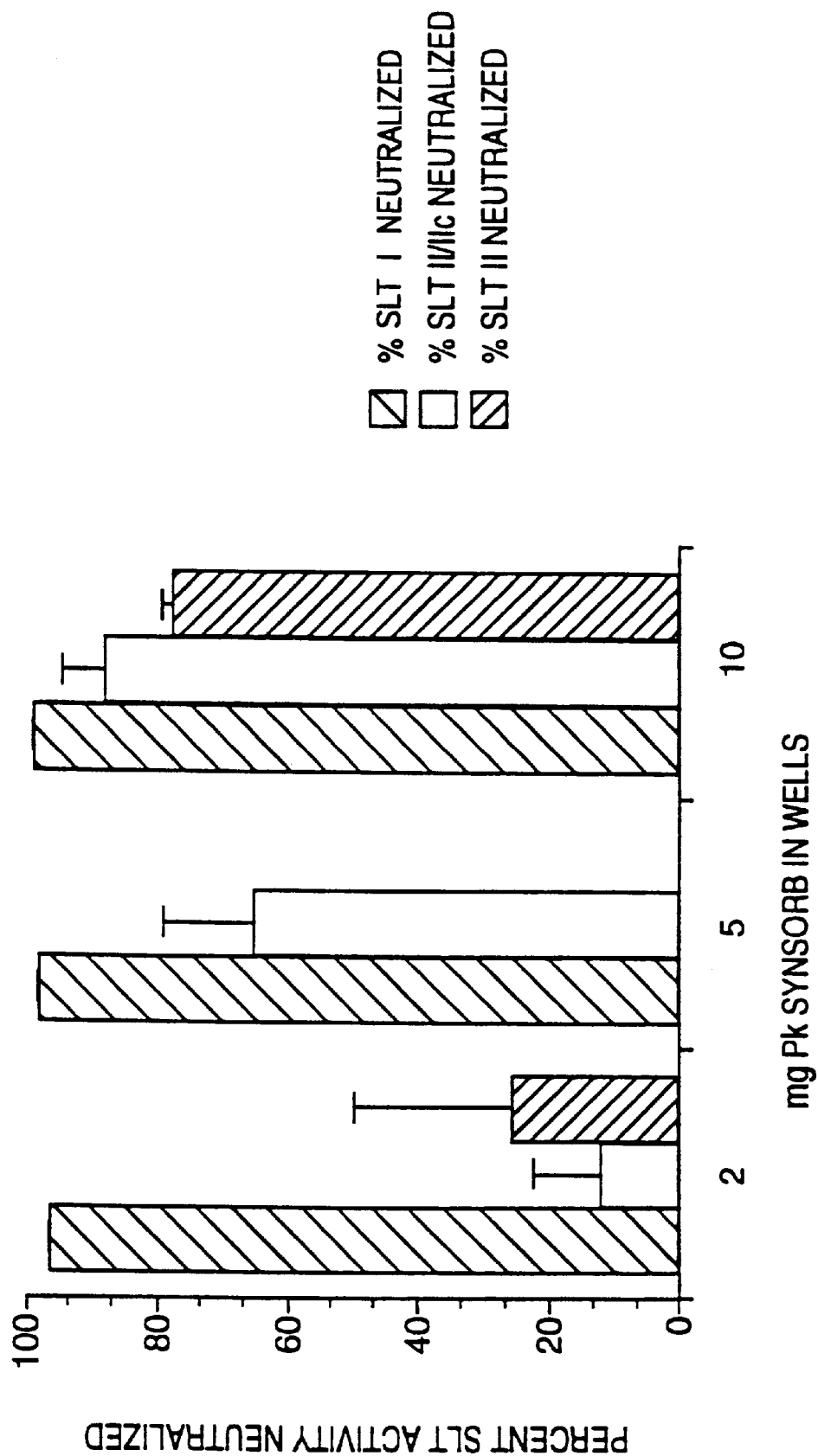

FIG. 5 demonstrates that >90% SLTI, SLTII/IIc and SLTII activity was neutralized by co-incubation of Vero cells and SLT extracts for three days, with as little as 10 mg of $P_k$ trisaccharide SYNSORB.

The subunit is bound preferably through a linking arm such as that described by Lemieux, R. U., et al., *J Am Chem Soc.* (1975) 97:4076–4083; to a solid, inert support that can be easily eliminated from the gastrointestinal system. An inert silica matrix embodiments of which are commercially available as "SYNSORB™" are preferred.

MODES OF CARRYING OUT THE INVENTION

The compositions useful in the conduct of the methods of the invention include a αGal(1–4)βGal disaccharide subunit, preferably the αGal(1–4)βGal (1–4)βGlcNAc trisaccharide subunit or αGal(1–4)βGal (1–4)βGlc trisaccharide subunit, preferably at the non-reducing terminus of an oligosaccharide. The di- and trisaccharides may be provided as a portion of a larger oligosaccharide coupled to a solid support or coupled directly, preferably through a linking arm such as that described by Lemieux, R. U., et al., *J Am Chem Soc* (1975) 97:4076–4083. The di- and trisaccharide subunits may also be coupled directly to pharmaceutically acceptable carriers or constitute a portion of an oligosaccharide coupled to such carriers. Depending on the application for which the compositions of the invention are suggested, the composition is designed to accommodate the di- or trisaccharide subunits so as advantageously to be employed in these applications.

As used herein, "shiga-like toxin" or "SLT" refers to group of toxins produced by enterohemorrhagic *E. coli* that resemble the Shigella-produced shiga toxins as is commonly understood in the art. These toxins comprise an enzymatically active A subunit and a multimeric receptor binding B subunit. Such SLTs include SLTI and the various grouped toxins designated in the art SLTII.

Rapid, tight binding of SLT's to $P_1$ disaccharide, $P_1$ trisaccharide or $P_k$ trisaccharide is demonstrated by the verocytoxicity neutralization and $I^{125}$ binding assays contained herein. SYNSORB™ bearing haptens, e.g., the $G_{M1}$ ganglioside Neu5Ac(2–3)βGal(1–4)βGlc and heat labile toxin from enterotoxigenic *E. coli*, would be expected to behave similarly. A single SYNSORB™ bearing several haptens with specificity for the different binding subunits of several different gastrointestinal infections should now be possible. Such universal SYNSORB™s would provide rapid, simple simultaneous diagnosis of a variety of gastrointestinal disorders.

The SYNSORB™s employed were obtained from Chembiomed (Edmonton, Canada). In each case the 8-methoxycarbonyloctyl glycoside of the respective hapten is activated and ligated to a silylaminated solid support followed by acetylation of the remaining amine groups on the solid support. These formulations are sold commercially as "SYNSORB™"s:

"$P_1$-di," which contains 0.60 μmole/g αGal(1–4)βGal disaccharide;

"$P_1$-tri," which contains 0.91 μmole/g αGal(1–4)βGal (1–4)βGlcNAc trisaccharide;

"$P_k$-tri," which contains 0.74 μmole/g αGal(1–4)βGal (1–4)βGlc trisaccharide;

"Linear B like tri," which contains 0.47 μmole/g αGal (1–3)βGal(1–4)βGlcNAc trisaccharide;

"Linear B like di," which contains 0.66 μmole/g αGal (1–3)βgal disaccharide;

"Glucose mono," which contains 1.0 μmol B-glucose; 8-methoxycarbonyoctanol activated and ligated to the silylated solid support.

A major aspect of the invention is the rapid efficient binding of physiological concentrations of any SLT present in biological samples, thus permitting assay of quantities of these toxins. Typically, in view of the conditions with which these toxins are associated, the biological sample will be a stool sample. The sample is extracted and prepared using standard extraction techniques and the extract is contacted with a solid support derivatized to an affinity ligand, wherein the affinity ligand comprise the αGal(1–4)βGal disaccharide subunit, preferably the αGal(1–4)βGal(1–4)βGlcNAc trisaccharide subunit or αGal(1–4)βGal(1–4)βGlc trisaccharide subunit. Said contact may be in a batch treatment of sample extract with the solid support, or the solid support may be supplied as a chromatography column and the sample extract applied to the column under conditions wherein any SLT present in a sample is absorbed.

SLT may be measured directly on the surface of the SYNSORB™ using any suitable detection system. In one approach, monoclonal or polyclonal antibodies specific for SLT can be utilized to quantify the amount of SLT bound directly to SYNSORB™, labeled, for example, by radioactive, biotinylated, or fluorescent moieties. A wide variety of protocols for detection of formation of specific binding complexes analogous to standard immunoassay techniques is well known in the art.

Compositions containing the αGal(1–4)βGal disaccharide subunit, preferably the αGal(1–4)βGal (1–4)βGlcNAc trisaccharide subunit or αGal(1–4)βGal (1–4)βGlc trisaccharide subunit, that can also be used as therapeutic agents may be supplied wherein the disaccharide subunit or trisaccharide subunits or an oligomer saccharide containing it is coupled to a nontoxic carrier, such as a liposome, biocompatible polymer, or carrier analogous to the above-referenced SYNSORB™s.

Alternatively, the disaccharide or a larger moiety containing it as a subunit may be formulated in standard pharmaceutical compositions for administration to the patient. Typically, the patient will be afflicted with a diarrhetic condition, and the target SLT will be present in the intestinal tract. Thus, a suitable mode of administration is through oral administration or other means of direct application to the gastrointestinal tract. The correct dosage range will depend on the severity of the infection, the mode of administration, the mode of formulation, and the judgment of the attending practitioner.

Activity of the SLTs can be assayed by taking advantage of the toxicity of these compounds to Vero cells. Vero cells (ATCC CCL81) can be obtained from the American-Type Culture Collection, Rockville, Md. These are maintained at 37° C./5% $CO_2$ in minimal essential medium with Earl's salts (MEM, Gibco BRL, Gaithersburg, Md.) containing 3% fetal bovine serum (FBS). Confluent Vero cell monolayers are disrupted using 0.25% tissue-culture grade trypsin and approximately $10^5$ cells in 200 µl FBS-supplemented MEM are added to each well of a 96-well microtiter plate. The plates are incubated overnight at 37° C./5% $CO_2$.

The samples to be tested, and suitable controls are added to the various wells and the plates are incubated for 2–3 days at 37° C./5% $CO_2$. Cytotoxic effects are readily visible in successful candidate wells as compared to control wells. The results can be quantitated by aspirating the remaining liquid from each of the wells and fixing the Vero cells which remain viable with 95% methanol and staining with Geimsa stain. The results are recorded using a microtiter plate reader set at a wavelength of 620 nm, as described by Samuel, J. E., Infect Immun (1990) 58:611–618 (supra). The dilution of the candidate test solution. The dilution of samples resulting in 50% destruction ($CD_{50}$) of the monolayers is determined by extrapolation from the resulting Vero cell killing curves.

The following examples are intended to illustrate but not to limit the invention.

EXAMPLE 1

SYNSORB—Verocytotoxicity Neutralization Assays

E. coli strains 0157:H-(E32511), which produces SLTII/SLTIIc and 026:H11 (H19) which produces SLTI only, or strain C600(933W), which produces SLTII only, were grown overnight at 37° C. on tryptic soy broth (Difco, Detroit, Mich.) agar plates. Polymycin and lysozyme extracts were prepared as described previously [Karmali, M. A., et al., J Clin Microbiol (1985) 22:614–619 and Head, S., et al., Infect Immunol (1990) 58:1532–1537)].

The first neutralization assay was designed to test the ability of SYNSORBs to absorb SLT activity from the E. coli extracts. The assay involved incubating 1 mL of the E. coli extracts for 30 min. at room temperature in 1.5 mL microcentrifuge tubes (Fisher) with 2 to 50 mg SYNSORB on an end-over-end rotator. The tubes were then removed from the apparatus and after the SYNSORB had settled to the bottom (a few seconds), serial five-fold dilutions of the absorbed extracts were prepared in unsupplemented MEM. Twenty (20) µL of each dilution was added to the appropriate wells in 96 well microtiter plates containing Vero cells. Bacterial extracts to which no SYNSORB was added served as controls. Once cytotoxic effects became apparent (2 to 3 days in the incubator) the growth medium was aspirated from each of the wells and Vero cells which remained viable were fixed with 95% methanol and stained with Giensa stain (Fisher). The results were then recorded using a microtiter plate reader set at a wavelength of 620 nm as described previously [Samuel et al., Infect Immun. 58:611–618 (1990)]. The absorbance data were then plotted versus the logarithm of the extract dilution. The dilution of the extracts resulting in 50% destruction ($CD_{50}$) of the monolayers was determined by extrapolation from the resulting Vero cell killing curves. Individual experiments were always performed in duplicate and, unless otherwise indicated, repeated at least two times. The percentage of neutralization was computed from the equation: 100-(100[$CD_{50}$ oligosaccharide SYNSORB-treated extracted+$CD_{50}$ acetylated silylaminated (ASA) SYNSORB-treated extract]). The nonparametric Mann-Whitney test using the two-tailed statistic T was employed to compute the significance level of difference between groups of independent observations [Altman, D. G., Practical statistics for medical research, 1st ed. New York, Chapman and Hall: 179–228 (1991)].

Figure 1A:
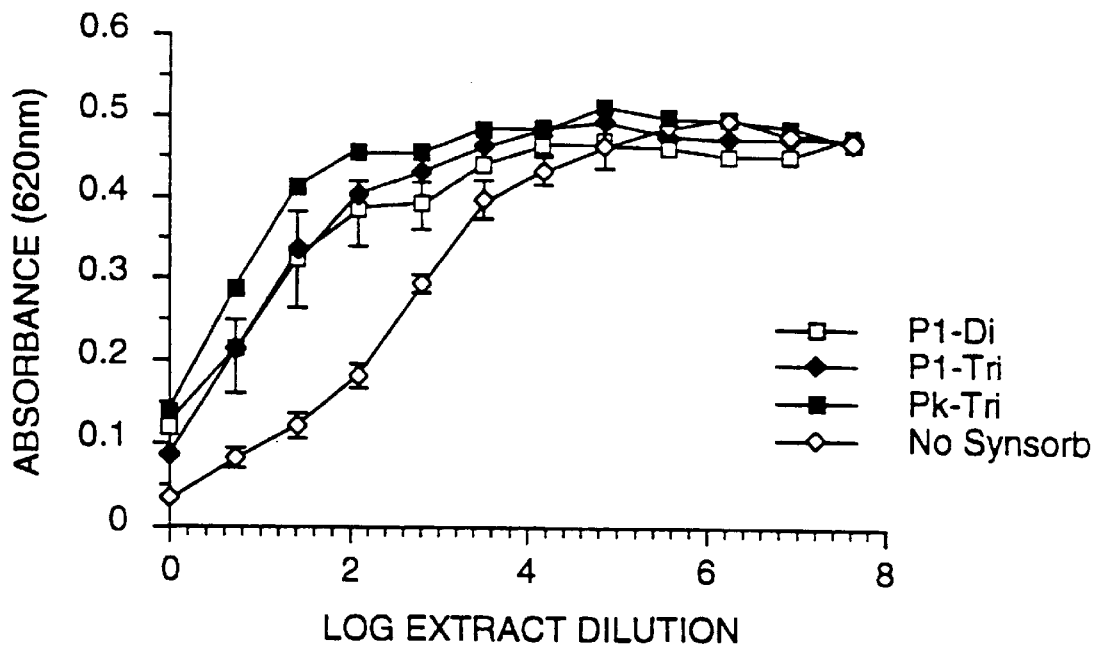
FIGS. 1A and B demonstrate the toxicity of bacterial extracts obtained using polymixin-B with respect to their ability to kill Vero cells in the presence and absence of various SYNSORBs.
Figure 1B:
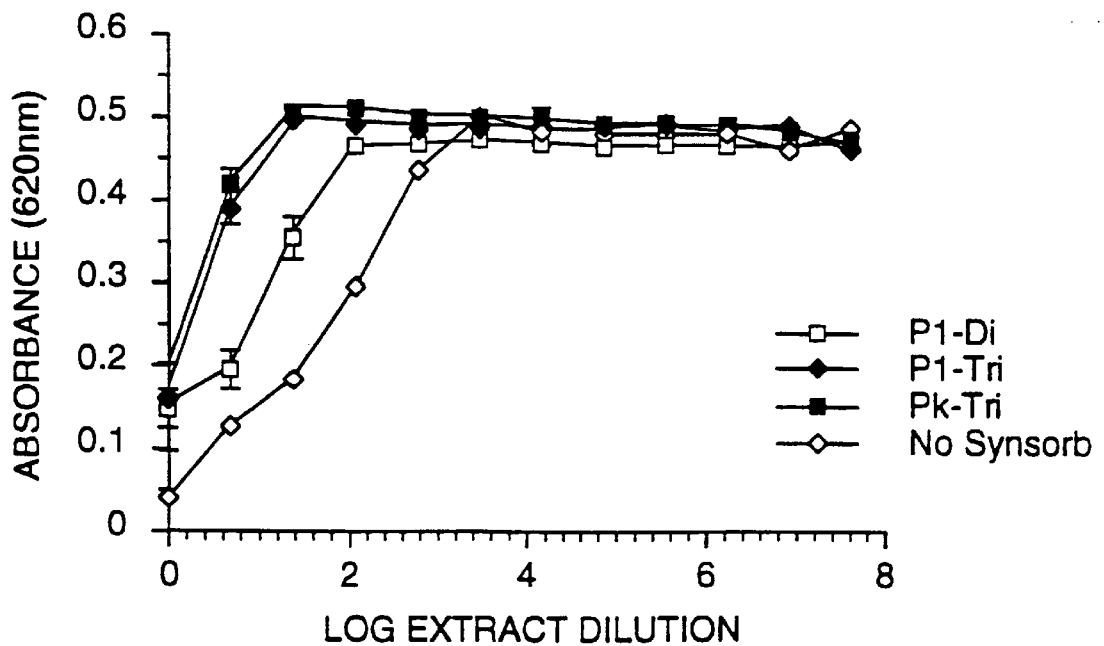
Figure 2A:
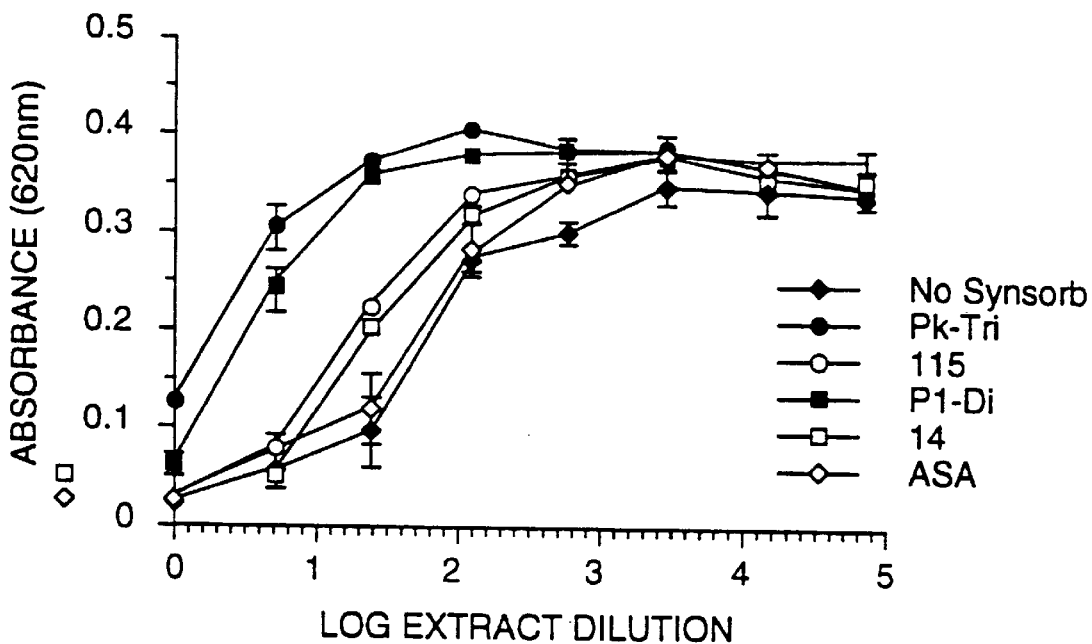
FIGS. 2A and B demonstrate the toxicity of bacterial extracts obtained using lysozyme with respect to their ability to kill Vero cells in the presence and absence of various SYNSORBs.
Figure 2B:
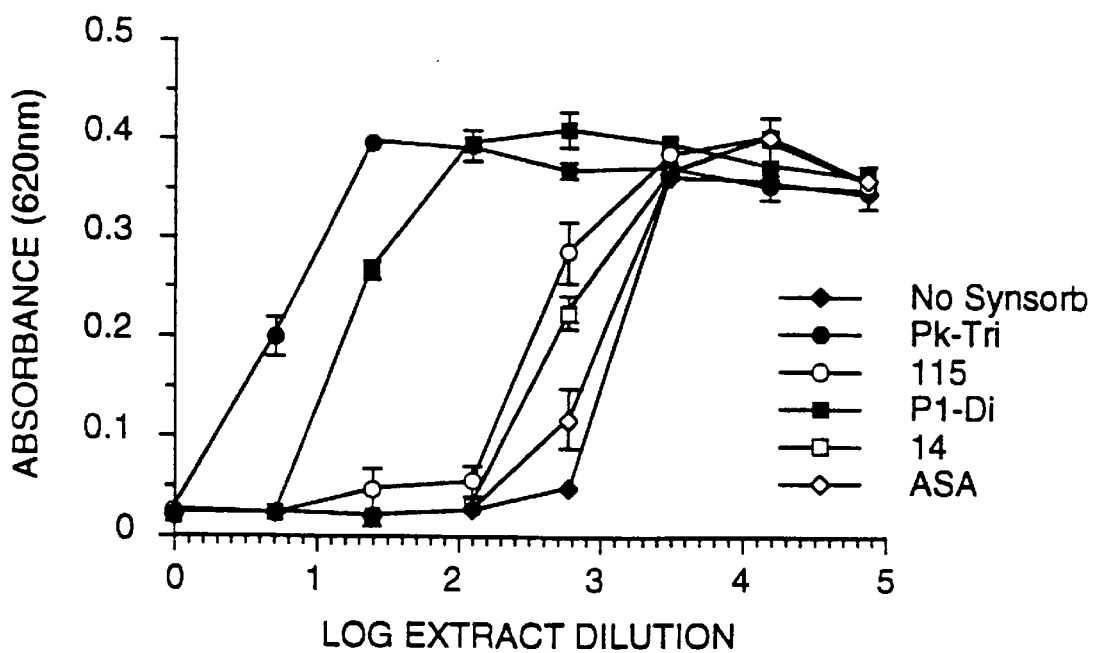

The second neutralization assay (co-incubation assay) was designed to test the ability of Pk trisaccharide SYNSORB to protect Vero cells from SLT activity over 3 days at 37° C. This assay involved incubating 180 µL of serial five-fold dilutions of polymyxin extracts in ethylene oxide-sterilized 1.5 mL microcentrifuge tubes each containing 2, 5 or 10 mg of Pk trisaccharide SYNSORB. After 1 h incubation with SYNSORB, the entire contents of each microcentrifuge tube were added to Vero cells monolayers in microtiter plates prepared as described above. The microtiter plates prepared as described above. The microtiter plates were then incubated at 37° C. for 3 days and the results of the experiment were recorded as described above (FIGS. 1 and 2).

Figure 3A:
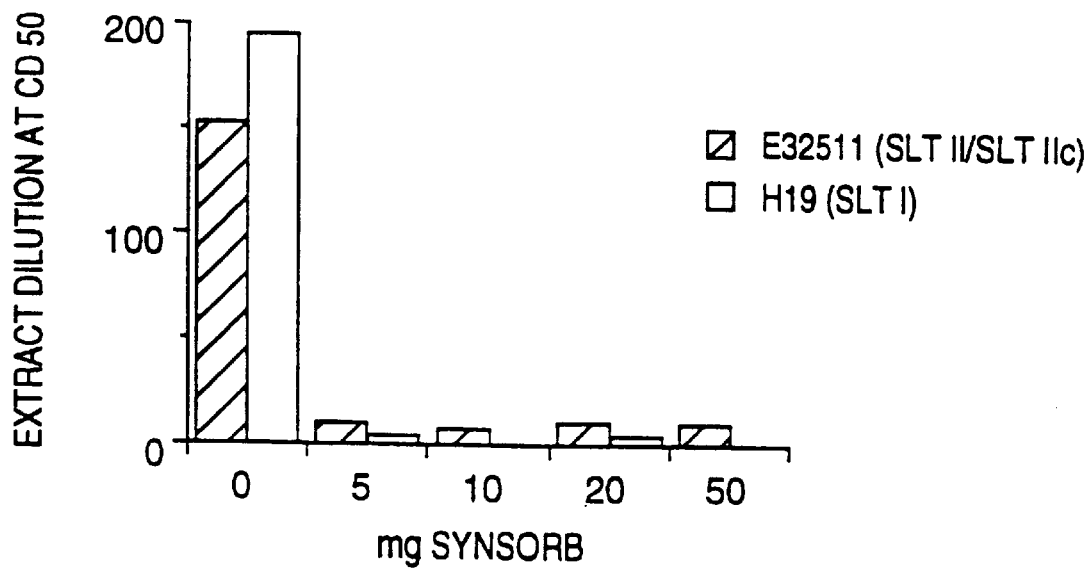
FIG. 3A demonstrates that as little as 10 mg of $P_k$ trisaccharide SYNSORB removes >90% SLT toxins from bacterial extracts.
Figure 3B:
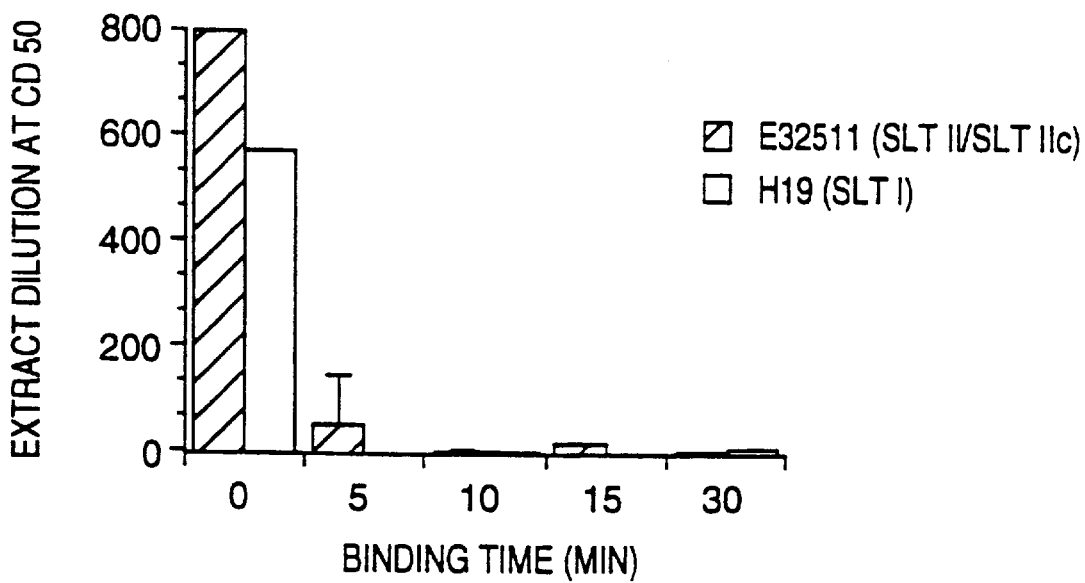

The foregoing determination was repeated using varying amounts of Pk-tri and various times of incubation, with the results shown in FIGS. 3A and 3B. As shown in FIG. 3A, as little as 5 mg SYNSORB was capable of neutralizing the activity of the extracts of both E32511 and H19 strains; similarly, as shown in FIG. 3B, only about 5 min incubation was required to achieve this result in either extract.

EXAMPLE 2

Iodinated SLT I Binding Assay

Purified SLTI was iodinated in 12×75 mm acid-washed glass culture tubes coated with 40 µg of Iodo Gen (Pierce Chemical Co., Rockford, Ill.). About 6 µg of purified SLTI was incubated for 1 min with 20 MBq $^{125}$-I labeled sodium iodide in 100 µl PBS. The reaction mixture was passed through a glass wool-plugged Pasteur pipette into 200 µl PBS containing a solution of cysteine (1 mg/ml) in PBS as described by Armstrong, G. D., et al., Infect Immunol (1987) 55:1294–1299. After 1 min, 200 µl of PBS containing 1% BSA was added to the mixture and the iodinated SLTI was purified by passing the solution through a 1 cm×30 cm Sephadex-G 25 gel filtration column with 0.1% BSA in PBS. The efficiency of the iodination reaction was determined by measuring the number of counts that were incorporated into trichloroacetic acid precipitated protein. Aliquots of the iodinated SLTI were stored at -90° C.

The assays were performed in PBS containing 0.1% BSA to reduce nonspecific binding. 2 mg of the various SYNSORBs were incubated for 30 on an end-over-end rotator with approximately 20,000 dpm of the iodinated SLTI prepared in Preparation B above (specific activity, 2.2×$10^7$ dpm/µg, $CD_{50}$ in the Verocytotoxicity assay, 0.4 pg/ml), in 0.5 ml PBS/BSA). The SYNSORBs were then washed with 3×1 ml portions of PBS BSA to remove unbound counts. The derivatized SYNSORBs were counted in an LKB Rackgamma model 1270 Gamma Counter.

The results are shown in Table 1.

TABLE 1

| SYNSORB | % SLTI Bound |
| --- | --- |
| Pk-tri | 93 |
| # 115 | 21 |
| Glc | 9 |
| ASA | 5 |

The SLT bound to Pk-tri SYNSORB could be partially released using 0.1 M acetic acid, 6 M guanidine HCl, or by heating in boiling water bath for 30 min in 10% SDS. However, neither 0.5 M lactose, 0.5 M galactose, or 0.2 M EDTA could displace the bound SLTI (FIG. 4).

Subsequent experiments showed that 2 mg of Pk-tri neutralized approximately 90% of the activity in *E. coli* H19 (SLTI) but about 10 mg Pk-tri SYNSORB was required to neutralize the activity of the *E. coli* 32511 (SLTII/SLTIIc) or *E. coli* C600/933W (SLTII) to a similar extent (FIG. 5).

We claim:

1. A pharmaceutical composition useful in treating enteric infections mediated by SLT which composition comprises as active ingredient a moiety comprising the disaccharide subunit αGal(1–4)βGal, which moiety is covalently attached to a solid inorganic support and which moiety is capable of binding SLT when so attached to said support, in admixture with a pharmaceutically acceptable excipient.

2. The pharmaceutical composition of claim 1 wherein said moiety comprises the trisaccharide subunit αGal(1–4)βGal(1–4)βGlcNAc or the trisaccharide subunit αGal(1–4)βGal(1–4)βGlc.

3. The pharmaceutical composition of claim 1 wherein said support is an inert silica matrix.

4. The pharmaceutical composition of claim 1 which is capable of being eliminated from the gastrointestinal tract.

5. The pharmaceutical composition of claim 1 wherein said moiety is attached to said support via a linker.

6. The pharmaceutical composition of claim 5 wherein said linker comprises a —$(CH_2)_8C(O)$— linking arm.

7. A pharmaceutical composition suitable for oral administration to a subject and which composition is useful in treating enteric infections medicated by SLT which composition comprises as active ingredient a composition comprising a pharmaceutically acceptable orally deliverable solid inert affinity support capable of being eliminated from the gastrointestinal tract which support has an affinity ligand covalently attached thereto through a spacer arm, which spacer arm is of corresponding length to —$(CH_2)_8C(O)$— and has a functional group at one terminus to react with said affinity ligand and a functional group at the other terminus to react with said support, wherein said ligand is an oligosaccharide comprising the disaccharide subunit αGal(1–4)βGal which binds the SLT in admixture with a pharmaceutically acceptable excipient.

8. The pharmaceutical composition of claim 7 wherein said oligosaccharide comprises the trisaccharide subunit αGal(1–4)βGal(1–4)βGlcNAc or the trisaccharide subunit αGal(1–4)βGal(1–4)βGlc.

9. The composition of claim 7 wherein said spacer arm corresponds to —$(Ch_2)_8C(O)$—.

10. A pharmaceutical composition useful in treating enteric infections mediated by SLT which composition comprises the trisaccharide subunit αGal(1–4)βGal(1–4)βGlc, wherein said subunit is covalently attached to an inert silica matrix via a —$(CH_2)_8C(O)$— linking arm, in admixture with a pharmaceutically acceptable excipient.

* * * * *